United States Patent [19]

Shiba et al.

[11] Patent Number: 4,755,179
[45] Date of Patent: Jul. 5, 1988

[54] ABSORBENT ARTICLE

[75] Inventors: Daisuke Shiba; Akira Sakurai, both of Utsunomiya, Japan

[73] Assignee: Kao Corporation, Tokyo, Japan

[21] Appl. No.: 886,900

[22] Filed: Jul. 18, 1986

[30] Foreign Application Priority Data

Jul. 19, 1985 [JP] Japan .................................. 60-159560

[51] Int. Cl.$^4$ ............................................. A61F 13/16
[52] U.S. Cl. ..................................... 604/370; 604/372
[58] Field of Search ............... 604/372, 370, 368, 366, 604/367

[56] References Cited

U.S. PATENT DOCUMENTS

| | | | |
|---|---|---|---|
| 4,216,772 | 8/1980 | Tsuchiya et al. | 604/372 |
| 4,364,992 | 12/1982 | Ito et al. | 604/368 |
| 4,405,324 | 9/1983 | Cruz, Jr. | 604/368 |
| 4,405,325 | 9/1983 | Antlfinger et al. | 604/370 |
| 4,417,893 | 11/1983 | Mizutani et al. | 604/370 X |
| 4,480,000 | 10/1984 | Watanabe et al. | 604/370 X |
| 4,603,070 | 7/1986 | Steel et al. | 604/370 X |

Primary Examiner—John D. Yasko
Attorney, Agent, or Firm—Birch, Stewart, Kolasch & Birch

[57] ABSTRACT

An absorbent article comprises a non-woven fabric sheet to come in contact with the skin of a user and an absorbent layer provided under said non-woven fabric sheet, said non-woven fabric sheet comprising polyester oligomer fibers having a hydrophilic group at least on the surface side to come into contact with the skin of a user so that said surface gets hydrophilic.

3 Claims, 1 Drawing Sheet

ABSORBENT ARTICLE

The present invention relates to a disposable absorbent article excellent in absorptivity, and particularly to an absorbent article such as a sanitary napkin or a paper diaper.

STATEMENT OF PRIOR ARTS

A conventional absorbent article such as a sanitary napkin or a paper diaper basically comprises an absorbent layer made of cotton pulp or absorptive paper, a leak-proof layer provided under the lower surface and side faces thereof if necessary, and a non-woven fabric mounted on the other surface thereof.

Various performance characteristics are required of the non-woven fabric constituting the surface layer of the absorbent article. Among them, the absorption performance necessary for conducting urine or menstrual blood to the absorbent layer is indispensable.

In a non-woven fabric that has been employed in the conventional absorbent article, the absorption performance has been generally imparted by using a hydrophilic natural fiber represented by rayon. According to this method, the absorption speed on the surface of the non-woven fabric can be surely increased. On the other hand, since the hydrophilic natural fiber absorbs water to the depths of itself with a strong water retention thereof and with bulkiness markedly reduced in its wet state, stickiness on the surface of the fiber in contact with the skin and backflow from the absorbent layer to the skin are increased in end use of the article as a sanitary napkin or a paper diaper, presenting problems including worsened feeling in its use and appearance of the rash.

A dry process non-woven fabric mainly made of a synthetic fiber has recently been rapidly spread as the surface material of the absorbent article as mentioned above to gradually change for the better the above-mentioned problems of stickiness inherent in the non-woven fabric mainly made of a hydrophilic natural fiber and increased backflow. Since the conventional dry process non-woven fabric consisting of a hydrophobic fiber has a water repellency on the surface thereof, however, a liquid is liable to flow to a large extent, leading to frequent occurrence of leak. There is a design of a non-woven fabric having its surface made hydrophilic by treating its hydrophobic fiber with a surface active agent to suppress the liquid flow on the surface thereof. In the case of treatment with a surface active agent, however, the water resistance of the non-woven fabric is so poor that the hydrophlic character of the non-woven fabric in a portion where menstrual blood or urine has permeated is largely decreased, with the result that liquid flow is liable to easily occur in that portion when menstrual blood or urine is excreted for the second time. Thus, difficulty is experienced in maintaining the original performance during the use of the absorbent article by a user.

Thus, absorbent articles now commercially available do not seem to be composed of a non-woven fabric with a desired performance as mentioned above.

SUMMARY OF THE INVENTION

The method of treating a hydrophobic fiber with a surface active agent as mentioned just above secures such a merit of use of a dry process non-woven fabric mainly made of a synthetic fiber that stickiness as well as backflow occurs only to a small extent and bulkiness is not reduced even when it is wetted, and is suggestive of high effectiveness of the method of imparting a hydrophilic character to the surface of a hydrophobic fiber by any means in improving the effect of conducting water to an absorbent layer. It also teaches that the water resistance of the hydrophilicity-imparted surface of the hydrophobic fiber is strongly demanded in order to maintain the initial properties during the course of user's use of the absorbent article.

The treatment with a surface active agent is not the only method of imparting a hydrophlic character to the surface of a hydrophobic fiber. In fact, various fiber manufacturers have proposed a number of inventions concerning the hydrophlicity-imparting method of endowing the hydrophilicity-imparting treatment with a capacity of providing a sufficient water resistance in addition to impartation of a hydrophilic character to the surface of the hydrophobic fiber as well as the fiber made hydrophilic by any treatment. These type of fibers are regarded as being used in sports wears and bedding. On the other hand, no ideas of use of these special type of fibers in disposable sanitary articles have ever been hit upon because of a preconception that the disposable sanitary articles are discarded after use thereof for a very short period of time as opposed to such wears. Thus, no instances of use of them in sanitary napkins and paper diapers could be found.

In view of the above, the inventors of the present invention have intensively studied with a view to finding a non-woven fabric which can satisfy simultaneously contradictory properties, i.e. increased water-conducting performance and decreased backflow, for eliminating the defects of a non-woven fabric used as the surface material of the conventional absorbent article, while focusing their attention on the use of a hydrophilic fiber subjected on its surface to the above-mentioned hydrophilicity-imparting treatment capable of securing water resistance. As a result, they have completed the present invention.

The invention provides an absorbent article which comprises a non-woven fabric sheet to come in contact with the skin of a user and an absorbent layer provided under said non-woven fabric sheet, said non-woven fabric sheet comprising polyester oligomer fibers having a hydrophilic group at least on the surface side to come into contact with the skin of a user so that said surface gets hydrophilic.

It is preferable that said non-woven fabric sheet comprises 60 to 100 percent by weight of the polyester oligomer fibers and zero to 40 percent by weight of other fibers and said non-woven fabric sheet comprises said polyester oligomer fibers on the surface side and hydrophobic fibers on the inner side.

The article of the invention is alternatively defined to comprise a non-woven fabric to be in contact with the skin and an absorbent layer provided under said non-woven fabric, characterized in that said non-woven fabric comprises a polyester fiber having its surface made hydrophilic with a polyester oligomer containing hydrophilic groups.

In order that the non-woven fabric of the absorbent article quickly conduct a liquid such as a body fluid to the absorbent layer, it is required that the surface of the fiber constituting the non-woven fabric be hydrophilic at least when the absorbent article is formed from the non-woven fabric. On the other hand, since the bulkiness of the non-woven fabric must be kept sufficient even in a wet state in order to suppress stickiness and backflow from the absorbent layer, the inside of the fiber must be hydrophobic.

The fiber having a hydrophilic character in the surface thereof and a hydrophobic character in the inside thereof can be obtained by imparting a hydrophilic character to the surface of a hydrophobic synthetic fiber, examples of which include fibers of polyolefins such as polyethylene and polypropylene; and polyester, polyamide, and polyacrylonitrile fibers. Among these fibers, a polyester fiber, which can be subjected to various surface treatments, excellent in bulkiness, and inexpensive, is the most preferred.

The best method of treating the surface of a hydrophobic fiber to provide a durable hydrophilic character thereto is one comprising fixing a hydrophilicity-imparting agent having affinity for the base polymer constituting the hydrophobic fiber in the vicinity of the surface of the fiber. The most preferred hydrophilicity-imparting agents are hydrophilic group-containing oligomers stably bondable to the fiber in the vicinity of the surface thereof by co-crystallization. Among others, a hydrophilic group-containing polyester oligomer is the most preferred for a polyester fiber. In this case, the molecular weight of the oligomer unit is preferably 300 or more from the viewpoint of stability of bonding to the polyester fiber, while it is preferably 6,000 or less from the viewpoint of dispersibility in liquid. Examples of the hydrophilic group include hydratable polyoxyalkylene groups; acidic groups such as sulfonic, phosphonic, and carboxylic acid groups and their ionizable salts; nitrogen type basic salts or their ionizable salts. Among them, polyoxyalkylene groups are the most preferred.

In order that the non-woven fabric of the absorbent article exhibit an increased water-conducting effect and a feature of a decreased backflow from the absorbent layer, the non-woven fabric must be constituted with a fiber having a hydrophilic character in the surface thereof and a hydrophobic character in the inside thereof. However, the non-woven fabric is not necessarily constituted of 100% of such a fiber. It will suffice in the present invention if at least 60 wt. % of a polyester fiber having its surface made hydrophilic be included in the non-woven fabric. The balance of less than 40% may be constituted of a common hydrophobic fiber or a hydrophilic fiber such as rayon. The non-woven fabric used in the present invention may have either a single layer structure or a multi-layer structure with consideration to adequateness of the thickness in so far as it includes at least 60% of a fiber having a hydrophilic character in the surface thereof and a hydrophobic character in the inside thereof.

The conditions for most effectively exhibiting the above-mentioned features of the non-woven fabric used in the present invention will now be described in detail.

The thickness of the non-woven fabric is one of the big factors to backflow from the absorbent layer to the outside of the non-woven fabric. Specifically, when the thickness of the non-woven fabric is too small, the distance between the skin and the absorbent layer is so shortened during wearing of the absorbent article in a wet state thereof that the backflow in so increased as to deteriorate the feeling in the use of the article. On the contrary, with an increase in the thickness of the non-woven fabric, the backflow surely decreases. However, when the thickness of the non-woven fabric is more than is needed, the whole of the absorbent article comes to have such a thick form that problems of increased user's discomfort and increased manufacturing cost may ensue.

Thus, the thickness of the non-woven fabric must be in the most adequate range in consideration to the backflow, feeling in the use of the article, and manufacturing cost. Although the adequate thickness range may differ depending on the end use of the nonwoven fabric, the whole thickness, under a load of 2.5 g/cm$^2$, is desired to be in a range of 0.3 to 0.8 mm in the case of a sanitary napkin and 0.6 to 2.5 mm in the case of a paper diaper.

In order to provide the above-mentioned thickness to the non-woven fabric of the absorbent article, adequate choice of a fiber constituting the non-woven fabric and giving an adequate basis weight to the non-woven fabric are necessary. Firstly, as already described, a hydrophobic synthetic fiber having its surface made hydrophilic and little liability to the reduction in the bulkiness even in a wet state thereof must be used. The size of the fiber may be in a range of 1.5 to 6 deniers. This is because a fiber size of less than 1.5 deniers provides a difficulty in increasing the bulkiness of the whole of the non-woven fabric, while a fiber size of more than 6 deniers gives a stiff feeling to the whole of the non-woven fabric to the detriment of the hand. In general, an increase in the basis weight is satisfactory in giving bulkiness to a non-woven fabric, while consideration of the manufacturing cost tends to decrease the basis weight as much as possible. In view of this, the fiber is desired to have as high elasticity as possible. In order to meet this, avoidance of use of too fine a fiber and, instead, selection of a hollow fiber or a fiber sterically crimped may be recommendable. When consideration is given to water resistance controllability of the surface hydrophilicity-imparting treatment, cost reduction, easiness in providing high elasticity, processability in making a non-woven fabric etc., the most suitable fibers constituting a non-woven fabric are polyester and polyolefin fibers.

Since a low basis weight of the non-woven fabric generally provides a small thickness while a high basis weight provides a large thickness, there is an adequate range of the basis weight dependent on the end use. The basis weight as a whole is desired to be in a range of 10 to 30 g/m$^2$ in the case of use of a fiber as mentioned above in a sanitary napkin and 20 to 50 g/m$^2$ in the case of use of it in a paper diaper.

[EXAMPLES]

The following Examples will illustrate the present invention in more detail.

EXAMPLES 1 TO 19 AND COMPARATIVE EXAMPLES 1 TO 4

The performance characteristics of non-woven fabrics made of each of various fibers made hydrophilic and absorbent articles comprising the same were examined according to the following methods. The results are shown in Table 2.

Non-woven fabrics except for those of Comparative Examples 2 and 3 were of a single- or double-layer structure and prepared by a dry thermal bonding process with a hot-melt fiber as the binder. The non-woven fiber of Comparative Example 2 was a commercially available product prepared by a wet process, while that of Comparative Example 3 was a commercially available product prepared by a span bond process. The absorbent articles simulating sanitary napkin or a paper diaper were prepared from the non-woven fabrics as listed in Examples and Comparative Examples, and were used as samples. In Examples 1 to 17 and Comparative Examples 1 to 3, a non-woven fabric of a commercially available Lorie ® (a product of Kao Soap Co., Ltd.) was substituted with a non-woven fabric as listed in Table 2. In Examples 18 and 19 and Comparative Examples 4, a non-woven fabric of a commercially available Meries ® (a product of Kao Soap Co., Ltd.) was substituted with a non-woven fabric as listed in Table 2.

<Test Methods>

(1) Surface Liquid Flow: A test liquid was dropped on the surface of a sample inclined at an angle of 45° from 1 cm above the surface. The distance between the drop point and a point to which the liquid flowed along the surface of the non-woven fabric before complete absorption into the sample was measured. It was referred to as the first surface liquid flow. Subsequently, one minute after the dropping of the test liquid, a test liquid was dropped again at the same point as in the previous dropping. The manner of flow along the surface of the non-woven fabric was observed and evaluated on the basis of the following ratings. It was referred to as the second liquid flow.

O ... The manner of flow was substantially the same as in the first liquid flow and absorption occurred as soon as the liquid was dropped.

Δ ... Absorption finished as soon as the flow exceeded the region of the first liquid flow.

X ... The liquid flowed beyond the region wetted by the first liquid flow and absorption occurred in a portion of the non-woven fabric not yet wetted.

Samples providing a short first surface liquid flow and a rating of O or Δ for the second surface liquid flow do not show large side leak, and hence demonstrate a high durability that the surface hydrophilicity-imparting treatment can afford.

The dropping condition was 0.1 g/sec for samples simulating a sanitary napkin (Examples 1 to 17 and Comparative Examples 1 to 3) and 0.5 g/sec for samples simulating a paper diaper (Example 18 and 19 and Comparative Example 1 to 3).

(2) 10 cc of a test liquid was absorbed in a sample simulating a sanitary napkin, while 150 cc of a test liquid was absorbed in a sample simulating a paper diaper. After a given period of time, each sample was pressurized to measure an amount of the test liquid returned through the non-woven fabric from the inside thereof. As the amount of such return is smaller, the stickiness on the surface is less, the feeling in the use of the article is better, and the effect of sopping up is superior.

(3) Thickness: The thickness of the non-woven fabric (in dry and wet states) was measured under a load of 2.5 g/cm$^2$ by means of a thickness meter.

TABLE 1

| | Hydrophilicity-imparting agent | Fiber*[1] | Remarks |
|---|---|---|---|
| A | polyoxyalkylene group-containing polyester obligomer average molecular weight: 1,700 | PET(A), LPET(A) | The hydrophilicity-imparting agent was prepared in accordance with Example 7 of Japanese Patent Publication No. 10,794/1970. |
| B | carboxylate group-containing polyester oligomer average molecular weight: 1,100 | PET(B) | The hydrophilicity-imparting agent was prepared in accordance with Example 1 of Japanese Patent Publication No. 10,794/1970. |
| C | sulfonate group-containing polyester oligomer average molecular weight: 3,500 | PET(C) | The hydrophilicity-imparting agent was prepared in accordance with Example 1 of Japanese Patent Publication No. 10,794/1970. |
| D | phosphonate group-containing polyester oligomer average molecular weight: 5,100 | PET(D) | The hydrophilicity-imparting agent was prepared in accordance with Example 1 of Japanese Patent Publication No. 10,794/1970. |
| E | dimethylhydrazide group-containing polyester oligomer average molecular weight: 2,800 | PET(E) | The hydrophilicity-imparting agent was prepared in accordance with Example 3 of Japanese Patent Publication No. 10,794/1970. |
| F | poly(ethylene-N—methylimino)diacetate group-containing polyester oligomer average molecular weight: 1,800 | PET(F) | The hydrophilicity-imparting agent was prepared in accordance with Example 4 of Japanese Patent Publication No. 10,794/1970. |
| G | surface active agent | PP(G), LPP(G) | The surface active agent was a mixture of an alkyl sulfate and an alkyl phosphate |
| H | spinning oil only | PP(H), LPP(H), LPET(H) | |

Note
*[1]: A polyester fiber made hydrophilic was prepared in the following manner. A hydrophilicity-imparting agent was dispersed in a solvent. A commercially available PET fiber was immersed in the resulting dispersion, and was dehydrated and dried to provide a rate of adherent hydrophilicity-imparting agent of 0.3%. The heat treatment was then conducted at 140° C. for 30 minutes in the case of the hydrophilicity-imparting agents A to D, at 180° C. for 5 minutes in the case of the hydrophilicity-imparting agent E, and at 150° C. for 10 minutes in the case of the hydrophilicity-imparting agent F, except for LPET which was heat-treated at 70° C. for 30 minutes. Here, PET represents a polyester fiber, PP a polypropylene fiber, LPET a conjugated low melting polyester-polyester fiber ("Melt" (Unitika Ltd.)), and LPP a conjugated polyester-polypropylene fiber ("ES" (polypropylene fiber of Chisso Corporation)).

TABLE 2

| | Whole Basis weight g/m² | Obverse layer Basis weight g/m² | Fiber | Size d | Mixing rate % | Reverse layer Basis weight g/m² | Fiber | Size d | Mixing rate % | Surface liquid flow First mm | Second | Amount of backflow g | Thickness In dry state mm | Thickness In wet state mm |
|---|---|---|---|---|---|---|---|---|---|---|---|---|---|---|
| Ex. 1 | 18 | 8 | LPET(A) | 3 | 100 | 10 | LPP(G) | 3 | 50 | 25~35 | O | 1.4 | 0.51 | 0.50 |
| | | | | | | | PET(A) | 6 | 50 | | | | | |
| Ex. 2 | " | " | LPET(A) | 3 | 100 | " | LPP(G) | 3 | 30 | " | O | 1.5 | 0.48 | 0.48 |
| | | | | | | | PET(A) | 6 | 70 | | | | | |
| Ex. 3 | " | " | LPET(A) | 3 | 100 | " | LPP(G) | 3 | 10 | " | O | 1.8 | 0.54 | 0.53 |
| | | | | | | | PET(A) | 6 | 90 | | | | | |
| Ex. 4 | " | " | LPET(A) | 3 | 100 | " | PET(A) | 6 | 100 | " | O | 1.9 | 0.53 | 0.51 |
| Ex. 5 | " | " | LPET(A) | 3 | 100 | " | LPP(H) | 6 | 100 | 40~50 | Δ | 1.8 | 0.52 | 0.52 |
| Ex. 6 | " | " | LPET(H) | 3 | 70 | " | PET(A) | 6 | 100 | 40~60 | " | 0.6 | 0.52 | 0.49 |
| | | | LPET(A) | 3 | 30 | | | | | | | | | |
| Ex. 7 | " | " | LPET(H) | 3 | 50 | " | LPP(H) | 3 | 30 | 40~60 | " | 0.6 | 0.52 | 0.48 |
| | | | LPET(A) | 3 | 50 | | PET(A) | 6 | 70 | | | | | |
| Co. Ex. 1 | " | " | LPP(H) | 1.5 | 100 | " | LPP(H) | 3 | 30 | 150 or more | X | 1.0 | 0.49 | 0.48 |
| | | | | | | | PP(H) | 2 | 70 | | | | | |
| Ex. 8 | " | " | LPET(H) | 3 | 30 | " | LPP(H) | 3 | 20 | 25~35 | O | 1.5 | 0.53 | 0.51 |
| | | | LPET(A) | 3 | 70 | | PET(B) | 6 | 80 | | | | | |
| Ex. 9 | " | " | LPET(H) | 3 | 30 | " | LPP(H) | 3 | 20 | " | " | 1.3 | 0.52 | 0.51 |
| | | | LPET(A) | 3 | 70 | | PET(C) | 6 | 80 | | | | | |
| Ex. 10 | " | " | LPET(H) | 3 | 30 | " | LPP(H) | 3 | 20 | " | " | 1.5 | 0.50 | 0.48 |
| | | | LPET(A) | 3 | 70 | | PET(D) | 6 | 80 | | | | | |
| Ex. 11 | " | " | LPET(H) | 3 | 30 | " | LPP(H) | 3 | 20 | " | " | 1.3 | 0.52 | 0.51 |
| | | | LPET(A) | 3 | 70 | | PET(E) | 6 | 80 | | | | | |
| Ex. 12 | " | " | LPET(H) | 3 | 30 | " | LPP(H) | 3 | 20 | " | " | 1.3 | 0.49 | 0.48 |
| | | | LPET(A) | 3 | 70 | | PET(F) | 6 | 80 | | | | | |
| Ex. 13 | " | " | LPET(A) | 1.5 | 100 | 12 | LPP(G) | 3 | 30 | 20~30 | O | 2.5 | 0.43 | 0.25 |
| | | | | | | | rayon | 3 | 70 | | | | | |
| Co. Ex. 2 | 30 | 30 | rayon | 3 | 100 | | | | | 20~30 | O | 4.8 | 0.25 | 0.20 |
| Co. Ex. 3 | 20 | 20 | PP(H) | 2 | 100 | | | | | 150 or more | X | 1.8 | 0.30 | 0.30 |
| Ex. 14 | 13 | 5 | LPET(A) | 3 | 100 | 8 | LPP(G) | 3 | 20 | 25~35 | O | 1.6 | 0.33 | 0.32 |
| | | | | | | | PET(A) | 6 | 80 | | | | | |
| Ex. 15 | 30 | 10 | LPET(A) | 3 | 100 | 20 | LPP(G) | 3 | 20 | " | O | 1.5 | 0.77 | 0.75 |
| | | | | | | | PET(A) | 6 | 80 | | | | | |
| Ex. 16 | 18 | 5 | LPP(H) | 1.5 | 100 | 13 | LPET(A) | 3 | 30 | 20~30 | O | 0.8 | 0.51 | 0.50 |
| | | | | | | | PET(A) | 6 | 70 | | | | | |
| Ex. 17 | 20 | 20 | LPET(H) | 1.5 | 20 | | | | | 20~30 | O | 1.1 | 0.40 | 0.38 |
| | | | LPET(A) | 1.5 | 40 | | | | | | | | | |
| | | | LPET(A) | 3 | 40 | | | | | | | | | |
| Ex. 18 | 35 | 10 | LPET(H) | 1.5 | 20 | 25 | LPP(H) | 3 | 20 | 25~35 | O | 1.0 | 0.70 | 0.66 |
| | | | LPET(A) | 3 | 80 | | LPP(A) | 3 | 80 | | | | | |
| Ex. 19 | 50 | 15 | LPET(H) | 1.5 | 20 | 35 | LPET(A) | 3 | 100 | " | Δ | 0.9 | 2.33 | 2.31 |
| | | | LPET(A) | 3 | 80 | | | | | | | | | |
| Co. Ex. 4 | 18 | 8 | LPP(G) | 1.5 | 100 | 10 | LPP(G) | 3 | 40 | " | X | 0.8 | 0.40 | 0.39 |
| | | | | | | | PP(G) | 2 | 60 | | | | | |

[Effects of the Invention]

As can be understood from Examples 1 to 19, the absorbent articles using a non-woven fabric including a polyester fiber having its surface made hydrophilic with a hydrophilic group-containing polyester oligomer according to the present invention gave rise to decreased first and second surface liquid flow and decreased backflow from the inside thereof to the surface thereof.

On the other hand, in Comparative Examples 1 to 4, the absorbent articles were prepared using a non-woven fabric falling outside the scope of the present invention in the same manner as in Examples, and were examined as to surface liquid flow and backflow. The absorbent articles of Comparative Examples 1 and 3 consisting of 100% of a hydrophobic fiber treated with only a spinning oil and not treated with any surface hydrophilicity-imparting agent gave rise to complete flow of a test liquid along the surface thereof. The absorbent article of Comparative Example 4 was poor in the water resistance to unfavorably cause large second surface liquid flow because the surface of the fiber was treated with a surface active agent. The absorbent article of Comparative Example 2 consisting of 100% of rayon gave rise to notably increased backflow and showed intense stickiness. Besides, the thickness of the non-woven fabric in a wet state thereof was small as compared with those of other examples, and hence provided a poor voluminousness.

BRIEF DESCRIPTION OF THE DRAWING

Both

Figure 1:
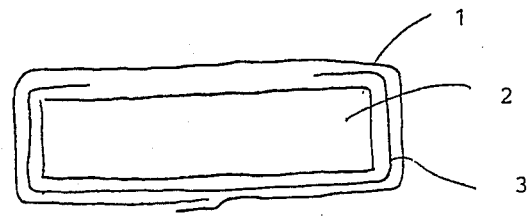
FIG. 1 and FIG. 2 illustrate examples of the absorbent article of the invention.
Figure 2:
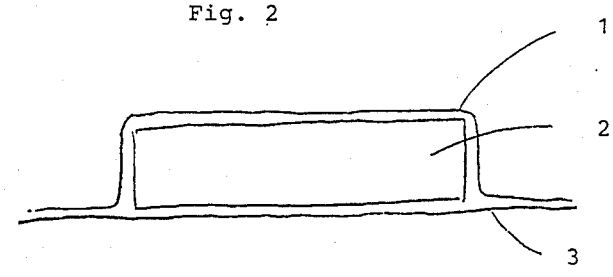

The invention can be worked in a variety of absorbent articles. The most preferable two constructions of the article are shown below in reference to the attached drawings. An article shown in FIG. 1 has a non-woven fabric sheet 1 of the invention, an absorbent layer 2 and a leak-proof back sheet 3, said non-woven fabric sheet envelopping over a whole the absorbent layer and the leak-proof back sheet, said back sheet envelopping the absorbent layer except for the surface of the skin-contacting side. Another example shown in FIG. 2 has a non-woven fabric sheet 1 of the invention, an absorbent layer 2 and a leak-proof back sheet 3, said absorbent layer having been inserted between said two sheets.

The embodiments of the invention in which an exclusive property or privilege is claimed are defined as follows:

1. An absorbent article having
a nonwoven fabric sheet which comes into contact with the skin of a user, and
an absorbent layer provided under said nonwoven fabric sheet,
said nonwoven fabric sheet comprising 60 to 100 percent by weight of polyester oligomer fibers and 0 to 40 percent by weight of other fibers,
said polyester oligomer fibers having an average molecular weight of 300 to 6,000 and having fixed on the surface of said fibers a hydrophilic group selected from the group consisting of a water-compatible polyoxyalkylene group, sulfonic acid group, phosphonic acid group, carboxylic acid group, and nitrogen basic salts thereof.

2. The absorbent article according to claim 1 wherein said hydrophilic group is a water-compatible polyoxyalkylene group.

3. The absorbent article according to claim 1 wherein said polyester oligomer fibers have a size of 1.5 to 6 deniers.

* * * * *